United States Patent [19]

Adams et al.

[11] Patent Number: 5,288,635
[45] Date of Patent: Feb. 22, 1994

[54] MICROBES AND THEIR USE TO DEGRADE N-PHOSPHONOMETHYLGLYCINE IN WASTE STREAMS

[75] Inventors: William J. Adams, St. Charles; Laurence E. Hallas, St. Louis; Michael A. Heitkamp, Ballwin, all of Mo.

[73] Assignee: Monsanto Company, St. Louis, Mo.

[21] Appl. No.: 544,436

[22] Filed: Jun. 27, 1990

[51] Int. Cl.$^5$ .............................. C02F 3/00; C12N 1/20
[52] U.S. Cl. ................... 435/262.5; 435/252.1; 435/252.4; 435/262
[58] Field of Search ............... 435/262, 252.4, 252.1, 435/262.5

[56] References Cited

U.S. PATENT DOCUMENTS 4,220,527  9/1980  Udaka et al. ................. 435/262 X
4,859,594  8/1989  Portier ......................... 435/172.1

OTHER PUBLICATIONS

G. S. Jacob, et al. *Applied and Environmental Microbiology*, vol. 54, No. 12 (Dec. 1988) pp. 2953-2958.
L. E. Hallas, et al. *Journal of Industrial Microbiology*, vol. 3 (1988) pp. 377-385.
T. M. Balthazor, et al., *Applied and Environmental Microbiology*, vol. 51, No. 2 (Feb. 1986) pp. 432-434.

*Primary Examiner*—Irene Marx
*Attorney, Agent, or Firm*—Frank D. Shearin

[57] ABSTRACT

A process is provided for the degradation of N-phosphonomethylglycine. A mixed culture of microorganisms (ATCC 55050) is attached to an inert, immobile support, and then contacted with an aqueous solution of N-phosphonomethylglycine for a sufficient time to degrade the N-phosphonomethylglycine. One of the microorganisms in the mixed culture was identified as *Moraxella anatipestifer* (ATCC 55051).

9 Claims, No Drawings

5,288,635

MICROBES AND THEIR USE TO DEGRADE N-PHOSPHONOMETHYLGLYCINE IN WASTE STREAMS

BACKGROUND OF THE INVENTION

This invention relates to microorganisms and their use to degrade N-phosphonomethylglycine in an aqueous solution, such as a waste stream, by biodegradation.

N-Phosphonomethylglycine, known in the agricultural chemical art as glyphosate, is a highly effective and commercially important phytotoxicant, useful in controlling the growth of germinating seeds, emerging seedlings, maturing and established woody and herbaceous vegetation, and aquatic plants. N-phosphonomethylglycine and its salts are conveniently applied in an aqueous formulation as a post-emergent phytotoxicant for the control of numerous plant species. N-phosphonomethylglycine and its salts are characterized by a broad spectrum activity, i.e., the control of a wide variety of plants.

Numerous methods are known in the art for the preparation of N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst consisting essentially of activated carbon. U.S. Pat. No. 3,954,848 to Franz disclose the oxidation of N-phosphonomethyliminodiacetic acid with hydrogen peroxide and an acid such as sulfuric acid. U.S. Pat. No. 4,670,190 to Kleiner discloses a process for the preparation of N-phosphonomethylglycine by reacting aminomethylphosphonic acid and glyoxylic acid in a molar ratio of about 1 to 2 in an aqueous medium or aqueous organic medium at temperatures between 30° and 100° C. These references are only illustrative since there are many other methods known in the art for preparing N-phosphonomethylglycine.

Regardless of the process by which N-phosphonomethylglycine is prepared, all of these processes produce aqueous, waste streams that contain small amounts of N-phosphonomethylglycine and various by-products and unreacted starting materials, such as N-phosphonomethyliminodiacetic acid, N-formyl-N-phosphonomethylglycine, aminomethylphosphonic acid, formaldehyde, and the like. Such waste streams should be kept to a minimum to help preserve the environment. (M. L. Rueppel, et al., "Metabolism and Degradation of Glyphosate in Soil and Water", *Journal of Agriculture and Food Chemistry*, Vol. 25 (1977) p. 517–522).

It is known that certain natural microorganisms will degrade N-phosphonomethylglycine over a period of time. In addition, several microorganisms have been isolated which will degrade N-phosphonomethylglycine. For example, G. S. Jacob, et al., "Metabolism of Glyphosate in Pseudomonas sp. Strain LBr", *Applied and Environmental Microbioloy*, Vol. 54, No. 12 (Dec. 1988) p 2953–2958, reports the metabolism of glyphosate by Pseudomonas sp. Strain LBr. L. E. Hallas, et al., "Characterization of Microbial Traits Associated with Glyphosate Biodegradation in Industrial Activated Sludge", *Journal of Industrial Microbiology*, 3 (1988) p 377–385 reports that the microorganisms from two industrial activated sludges that treat N-phosphonomethylglycine waste streams were enumerated by microscopic examination. It was suggested that the degradation activity is not a universal trait, and its expression requires enrichment through specific selective pressures. T. M. Balthazor, et al., "Glyphosate-Degrading Microorganisms from Industrial Activated Sludge", *Applied and Environmental Microbiology*, Vol. 51 No. 2 (Feb. 1986) p 432–434, discloses a plating medium to isolate microorganisms that will degrade N-phosphonomethylglycine as the sole phosphorus source. One purified isolate metabolized N-phosphonomethylglycine to aminomethylphosphonic acid was identified as a Flavobacterium species.

U.S. Pat. No. 4,859,594 discloses microorganisms separated from natural environments and purified and genetically modified, and a process for immobilizing these microorganisms by affixing them to substrates. The biocatalytic compositions are useful for the detoxification of toxin-polluted streams containing a wide class of toxicants.

Although the prior art discloses that certain microorganisms are effective for the degradation of N-phosphonomethylglycine, and that N-phosphonomethylglycine can be biodegraded in an industrial pond, such biodegradation requires a significant amount of time to achieve substantial degradation of the N-phosphonomethylglycine. Now there is provided a mixture of microorganisms that have been conditioned to degrade N-phosphonomethylglycine and their use to degrade N-phosphonomethylglycine in a very short period of time and with a high degree of effectiveness.

SUMMARY OF THE INVENTION

These and other advantages are achieved with microorganisms, suitable for biologically degrading N-phosphonomethylglycine having an American Type Culture Collection number 55050, which are useful in a process to biologically degrade N-phosphonomethylglycine in an aqueous solution which comprises contacting the aqueous solution with immobilized microorganisms having an American Type Culture Collection accession number of 55050 for a sufficient time to degrade a substantial portion of the N-phosphonomethylglycine.

DETAILED DESCRIPTION OF THE INVENTION

Since it is known that certain microorganisms are effective in the degradation of N-phosphonomethylglycine, and particularly the microorganisms that exist in the waste treatment pond at Monsanto Company's N-phosphonomethylglycine manufacturing facility located at Luling, La., a colony of microorganisms containing approximately 40 species of microorganisms was obtained from the waste treatment pond. These were obtained as sludge samples from the pond, and the sludge was used to establish a bioreactor which was continuously mixed, aerated, routinely titrated to pH 7, and fed nutrients in an aqueous solution containing increasing amounts of N-phosphonomethylglycine. Inorganic nitrogen was ammended into the bioreactor by the addition of ammonium nitrate. The degradation of N-phosphonomethylglycine, the production of aminomethylphosphonic acid and the pH were monitored in the bioreactor. When the N-phosphonomethylglycine was degraded, the bioreactor was allowed to settle for two hours, and 80% of the liquid volume was discarded. The bioreactor was then refilled by metering in fresh aqueous solution over a four-hour time interval containing up to 2200 milligrams per liter of N-phosphonomethylglycine until degradation of N-phosphonomethylglycine was achieved in the bioreactor.

After the colony of microorganisms was conditioned to accept high loadings of N-phosphonomethylglycine, the colony was then placed on a immobilized carrier by techniques known to those skilled in the art.

The solid substrate of the carrier to which the microorganisms of this invention are attached is porous, and preferably of pore volume of at least 0.2 microns/gram of solids material. Preferably, the pore volume ranges from about 0.2 microns/gram to about 45 microns/gram, more preferably from about 5 microns/gram to about 15 microns/gram of solids material. Particle sizes range generally from about 0.5 mm to about 2.0 mm, preferably from about 0.75 mm to about 1.0 mm, in diameter. Biocatalyst formed on such substrates are employed as fixed beds. The biocatalyst particles are sized in accordance with accepted engineering principles to provide good contact between the effluent and the carrier. Greater details on such solid substrates are described in U.S. Pat. No. 4,775,160 and U.S. Pat. No. 4,859,594.

Solid surfaces to which the microorganisms can be affixed are, preferably an aminopolysaccharide surface such as chitan, chitosan, n-carboxychitosan, cellulose, or a porous inorganic oxide, such as alumina, silica, silica-alumina, clay, diatomaceous earth or the like. A preferred support is one wherein the chitin, or chitosan is dispersed upon a second solid support, e.g., a porous substrate. The classes of useful porous substrates is quite large, exemplary of which are, e.g., (1) silica or silica gel, clays, and silicates including those synthetically prepared and naturally occurring, for example, attapulgus clay, china clay, diatomaceous earth, fuller's earth, kaolin, kieselguhr, etc.; (2) ceramics, porcelain, crushed firebrick, bauxite; (3) synthetic and naturally occurring refractory inorganic oxides such as alumina, titanium dioxide, zirconium dioxide, chromium oxide, zinc oxide, magnesia, thoria, boria, silica-alumina, silica-magnesia, chromiaalumina, alumina-boria, silica-zirconia, silica carbide, boron nitride, etc.; and (4) crystalline zeolitic alumino-silicates such as naturally occurring or synthetically prepared mordenite and/or faujasite. Diatomaceous earth provides satisfactory results, and this is what we prefer to use.

The solid support surface to which the microorganisms are affixed can be used advantageously in the method of this invention in any configuration, shape, or size which exposes the microorganism disposed thereon to the effluent to be treated. The choice of configuration, shape, and size of the refractory inorganic oxide depends on the particular circumstances of use of the method of this invention. Generally, the support surface can be conveniently employed in particulate form, as pills, pellets, granules, rings, spheres, rods, hollow tubes, and the like. Granules are readily available commercially, and these are preferred.

As will occur to those skilled in the art, the vessel containing the carrier with the deposited microorganisms can be of any size or shape, depending on factors such as the volume of liquid to be treated, the concentration of N-phosphonomethylglycine in the aqueous stream, and the like. It is only necessary that the vessel is designed to permit contact of the aqueous stream with the microorganisms for a sufficient time to degrade the N-phosphonomethylglycine, which is usually about 10–30 minutes under optimum conditions, to achieve greater than 90 percent degradation of the N-phosphonomethylglycine.

The microorganisms that have been conditioned to degrade N-phosphonomethylglycine are important in the process of the present invention. The culture of microorganisms containing approximately 40 species obtained from the waste treatment pond at Luling, La., were conditioned to degrade 200 milligrams per liter of N-phosphonomethylglycine, and thereafter, a sample was submitted to the American Type Culture Collection and assigned ATCC 55050. The species of microorganisms remaining after conditioning is unknown, and all of the species that degrade N-phosphonomethylglycine is also unknown. The predominate characteristics of the culture are set forth in Table 1.

TABLE 1

PREDOMINANT METABOLIC CHARACTERISTICS IN ACTIVATED SLUDGE MICROORGANISMS (ATCC 55050)

| Trait | % Presence* |
|---|---|
| Fermentation | |
| D-Arabitol | 93 |
| D-Turanose | 96 |
| Trehalose | 96 |
| Saccharose | 96 |
| Maltose | 96 |
| Mannitol | 95 |
| Inositol | 95 |
| L-Fructose | 99 |
| D-glucose | 99 |
| Adonitol | 99 |
| Arginine | 94 |
| Glycerol | 100 |
| N-Acetylglucosamine | 95 |
| Enzymatic | |
| α-glucosidase | 97 |
| Gly Aminopeptidase | 100 |
| Glucosaminidase | 96 |
| Arg Aminopeptidase | 100 |
| Leu Aminopeptidase | 100 |
| Alkaline Phosphatase | 99 |

*A predominant characteristic was defined as occurring in >90% of the microbes.

One microorganism that had a high degree of degrading activity toward N-phosphonomethylglycine in the conditioned colony was isolated an identified on a Biolog, In. (Hayward, Calif.) GN Microlog plate. This gram negative, rod-shaped microorganism is characterized as *Moraxella anatipestifer* (ATTC 55051). The characteristics of this microorganism is set froth in Table 2.

TABLE 2

Identifying Metabolic (Biodegradation) Characteristics of *Moraxella Anatipestifer* (ATCC 55051)

| | |
|---|---|
| Dextrin | D-Galactonic Acid Lactone |
| Glycogen | D-Galacturonic Acid |
| | D-Gluconic Acid |
| Tween 40 | D-Glucosaminic Acid |
| Tween 80 | D-Glucuronic Acid |
| Adonitol | α-Keto Glutaric Acid |
| L-Arabinose | D,L-Lactic Acid |
| D-Arabitol | Propionic Acid |
| Cellobiose | Succinic Acid |
| I-Errthyitol | Bromosuccinic Acid |
| D-Fructose | Alaninamide |
| L-Fucose | D-Alanine |
| D-Galactose | L-Alanine |
| Gentiobiose | L-Alanylglycine |
| α-D-Glucose | L-Asparagine |
| M-Inositol | L-Aspartic Acid |
| α-Lactose | L-Glutamic Acid |
| Maltose | Glycyl-L-Aspartic Acid |
| D-Mannitol | Glycyl-L-Glutamic Acid |
| D-Mannose | Hydroxy L-Proline |
| Psicose | L-Ornithine |

TABLE 2-continued

Identifying Metabolic (Biodegradation) Characteristics of
*Moraxella Anatipestifer* (ATCC 55051)

| L-Rhamnose | L-Proline |
| --- | --- |
| Sucrose | D-Serine |
| Turanose | L-Serine |
| Methylpyruvate | L-Threonine |
| Mono-Methyl Succinate | D,L-Carnitine |
| Cis-Aconitic Acid | α-Amino,Butyric Acid |
| Citric Acid | |

A culture of the microorganism and the conditioned colony has been deposited in the American Type Culture Collection at Rockville, Md., and each culture assigned an identifying member, each as previously identified, this depository affording permanence of the deposit and ready accessibility thereto by the public on grant of a patent, and under conditions which assure (a) that access to the culture will be available during pendency of the patent application to one determined to be entitled thereto under 37 CFR 1.14 and 35 USC 122, and (b) that all restrictions on the availability to the public of the culture so deposited will be irrevocably removed upon grant of a patent.

The invention is further illustrated by, but not limited to, the following examples.

EXAMPLE 1

A culture of microorganisms was obtained in a sludge sample taken from the waste treatment pond at Monsanto Company's facility located at Luling, La. The sludge was used to establish a bioreactor which was continuously mixed, aerated, routinely titrated to pH 7, and fed an aqueous solution containing N-phosphonomethylglycine ranging from 500-2000 milligrams per liter. The degradation of N-phosphonomethylglycine, the production of aminomethylphosphonic acid and the pH were monitored in the bioreactor. When the N-phosphonomethylglycine was completely degraded, the bioreactor was allowed to settle for two hours, and 80% of the liquid volume was discarded. The bioreactor was then refilled by metering in fresh aqueous solution over a four-hour time interval containing up to 2200 milligrams per liter of N-phosphonomethylglycine. Inorganic nitrogen was ammended into the bioreactor by the addition of 50 milligrams per liter of ammonium nitrate. This was continued until degradation of N-phosphonomethylglycine was achieved in the bioreactor.

After the culture of microorganisms was conditioned to accept high loadings of N-phosphonomethylglycine, the colony was then placed on an immobilized carrier contained in a cell column. The column consisted of an acrylic tube 60 centimeters (24 in.) long having an internal diameter of 8 centimeters (3.25 in.) with a wall thickness of 0.625 centimeters (0.25 in.). An acrylic collar was fused onto the bottom of the tube and an identically sized acrylic collar was placed around a 350 ml buchner funnel containing a glass frit of medium porosity (Corning Glass Works No. 36060). The glass funnel was attached to the plastic tubes by using C-clamps on the collars and tightening until the upper lip of the glass funnel sealed into a 0.625 cm (0.25 in.) thick rubber gasket. The glass frit served as the lower support for the biocarrier in the columns, and air was forced into the column through the funnel from the bottom.

A port for the inflow of waste consisted of a 1.6 cm (0.625 in.) hole bored through the plastic tubing 12.5 cm (5 in.) above the glass frit. The hole was sealed with a rubber stopper containing a 20 cm length (8 in.) of 0.625 cm (0.25 in.) stainless steel tubing containing a 90° bend at the midpoint. This feed tube discharged waste 2.5 cm (1 in.) above the glass frit. A second and third hole were bored 35 cm (14 in.) and 60 cm (24 in.) up the column from the frit and used as direct waste discharge ports for the packed column.

Immobilized cell columns were prepared by packing the plastic tubing to heights of 30 cm with a biocarrier, which was diatomaceous earth, identified as Manville R-635. The biocarrier was soaked overnight in an acidic chitosan solution, then rinsed in water, and the pH adjusted to 7.0 before addition to the column. Then, the culture of microorganisms which had been conditioned in the series of progressive steps as described above was added to the column to form a bioreactor. The bioreactor was continuously mixed, aerated, routine titrated to pH 7, and fed batches of aqueous solutions containing N-phosphonomethylglycine concentrations ranging from 500-2000 mg per liter. Glyphosate degradation, aminomethylphosphonic acid production and pH were monitored in the bioreactor.

An aqueous solution containing 400 mg per liter of N-phosphonomethylglycine was then pumped through the column at a rate of 3 ml per minute resulting in a retention time in the column of 350 minutes. Greater than 99% of the N-phosphonomethylglycine was degraded immediately. After 9 days of operating with this feedstock, the concentration of N-phosphonomethylglycine was increased to 1400 mg per liter, and the degradation activity dropped to about 85% after 5 days and returned to greater than 99% 2 days later. A significant increase in bacterial biomass was observed.

On day 27, the pumping rate was increased to 25 ml per minute (retention time 42 minutes), and within 4 days greater than 99% degradation activity was observed. High flow studies were then conducted preliminary to Example 2 pilot plant work. The biocarrier bed depth was reduced to 30 cm (12 in.) resulting in a lower retention time. The concentration of N-phosphonomethylglycine in the feedstock was lowered to 50 mg per liter in a stepwise fashion. Degradation activities of >98% to 82% were achieved at pumping rates of 25 ml per minute (retention time 23 minutes) and 30 ml per minute (retention time 19 minutes), respectively.

EXAMPLE 2

A culture (37.8 liters, 10 gallons) of microorganisms was obtained from a sludge sample taken from the Luling waste treatment pond. The sludge was used to establish a N-phosphonomethylglycine degrading activity similar to that described in Example 1. When the activity was established, the enriched sludge was transferred to a drum (208 liters, 55 gallons) containing 45.5 kg, 100 pounds of R-635 solid support as in Example 1. A center well was created in the middle of the drum using a washing tube (10 cm ID) with a perforated bottom. The biocarrier, sludge and aqueous solution containing N-phosphonomethylglycine (500 mg per liter) surrounded the center tube. The aqueous solution was circulated through the carrier bed by pumping liquid from the bottom of the center well to the top of the drum; an air sparger provided oxygen. When N-phosphonomethylglycine degradation was complete, the solution was drained from the drum and fresh solution was added.

A pilot plant containing an equalization tank (1900 liter) and a packed bed column (2.74×7.3 meters) configured in an upflow mode was prepared. Separate lines sparged air and fed an aqueous solution containing N-phosphonomethylglycine and ammonium nitrate to the tank. The pH was controlled in the equalization tank as in Example 1. Approximately 900 kg (2000 pounds) of fresh carrier was intermingled with the acclimated carrier containing N-phosphonomethylglycine degrading microorganisms. Steps were taken to promote microbial growth throughout the biocarrier as in Example 1. Initially, the aqueous solution was recirculated (18.9 liters per minute) in the column with pH control. After N-phosphonomethylglycine disappeared, fresh aqueous solution containing yeast extract (25-50 mg per liter) was added. Treatment performance was monitored by analyses of oxygen, pH, and temperature. Mechanical performance was monitored by analyses of water and air flow rate, and pump operation.

Continuous flow operation was begun after the biocarrier acclimated to 500 mg/l N-phosphonomethylglycine degradation. Initially, an aqueous solution containing 50 mg/l of N-phosphonomethylglycine and 25 mg/l of inorganic nitrogen was pumped through the column at 3.78 liters per minute (100 minute retention time). The detection limit for N-phosphonomethylglycine was 3-5 mg/l so 90-95% degrading activity could be confirmed. Optimal performance was established over the next 35 days through several operational and mechanical changes. The flow rate was increased to 19 liters per minute (20 minute retention time). Yeast extract was occasionally added to promote microbial growth. It was also found that a pH increase of between 1-1.5 units was critical to good degrading activity. Finally, a fluidization of the column was accomplished using a 378 liter per minute pump. This removed excess sludge and stabilized N-phosphonomethylglycine degradation.

A second 30-day period was used to establish a maximum loading rate for N-phosphonomethylglycine. Three step flow rate increases were accomplished resulting in 15, 10, and 8 minute retention times. The 8-minute retention time produced some degradation activity. However, the 10-minute retention time (144 hydraulic turnovers per day) maintained a consistent >90% N-phosphonomethylglycine degrading activity.

A viability and surge test was also performed to test the resilience of the immobilized microorganisms. The flow rate was slowed to 3.78-11.3 liters per minute, and no chemical amendments on pH control occurred for 21 days. At that time, the flow rate was increased to 37.8 liters per minute (10-minute retention time). The N-phosphonomethylglycine level was increased to 50 mg/l over 5 days. Two days were required to initiate a degrading activity and an additional 2 days were needed before >90% N-phosphonomethylglycine removal was seen.

A sample of the conditioned sludge was taken from the solid support. It was placed in a mineral salts medium (as described by T. M. Balthazor, et al.) containing approximately 200 mg/l of N-phosphonomethylglycine. After the compound was biologically degraded, the sample was split. One-half of the sample was submitted as a mixed culture to the American Type Culture Collection and assigned ATCC 55050. The other half of the sample was separated into individual microorganisms using standard techniques. One culture exhibiting high degrading activity was identified and submitted to the American Type Culture Collection. It was *Moraxella anatipestifer* (ATCC 55051).

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

What is claimed is:

1. An isolated mixed culture of microorganisms ATCC 55050.

2. A biologically pure culture of a microorganism *Moraxella anatipestifer* ATCC 55051.

3. A process for the degradation of N-phosphonomethylglycine which comprises attaching a mixed culture of microorganisms ATCC 55050 to an inert, immobile support, and contacting an aqueous stream containing the N-phosphonomethylglycine with the microorganisms on the immobile support for a sufficient time to degrade the N-phosphonomethylglycine.

4. A process of claim 3 wherein one of the microorganisms in the mixed culture is *Moraxella anatipestifer* ATCC 5505.

5. A process of claim 3 wherein greater than 90 percent of the N-phosphonomethylglycine is degraded.

6. A process of claim 3 wherein the aqueous stream containing the N-phosphonomethylglycine is contacted with the support containing the attached microorganisms for less than 30 minutes.

7. A process of claim 6 wherein the contact time is less than 20 minutes.

8. A process of claim 3 wherein the mixed culture of microorganisms is attached to an inert support of diatomaceous earth.

9. A process of claim 8 wherein the diatomaceous earth is soaked in a solution of chitosan or chitin before the microorganisms are attached thereto.

* * * * *